United States Patent
Parihar

(10) Patent No.: US 9,451,937 B2
(45) Date of Patent: Sep. 27, 2016

(54) PERCUTANEOUS INSTRUMENT WITH COLLET LOCKING MECHANISMS

(71) Applicant: Ethicon Endo-Surgery, Inc., Mason, OH (US)

(72) Inventor: Shailendra K. Parihar, Mason, OH (US)

(73) Assignee: Ethicon Endo-Surgery, LLC, Guaynabo, PR (US)

( * ) Notice: Subject to any disclaimer, the term of this patent is extended or adjusted under 35 U.S.C. 154(b) by 384 days.

(21) Appl. No.: 13/779,235

(22) Filed: Feb. 27, 2013

(65) Prior Publication Data

US 2014/0243868 A1   Aug. 28, 2014

(51) Int. Cl.
*A61B 17/00* (2006.01)
*A61B 17/29* (2006.01)

(52) U.S. Cl.
CPC ......... *A61B 17/00234* (2013.01); *A61B 17/29* (2013.01); *A61B 2017/00362* (2013.01); *A61B 2017/00473* (2013.01); *A61B 2017/00477* (2013.01); *A61B 2017/2931* (2013.01)

(58) Field of Classification Search
CPC ............ A61B 17/00234; A61B 17/29; A61B 2017/2931; A61B 2017/00477; A61B 2017/00362; A61B 17/3417; A61B 2017/00473; A61B 2017/294; A61B 2017/2946
USPC .............................................. 606/205–210, 1
See application file for complete search history.

(56) References Cited

U.S. PATENT DOCUMENTS

| | | | |
|---|---|---|---|
| 3,043,309 A | 7/1962 | McCarthy | |
| 3,358,676 A | 12/1967 | Frei et al. | |
| 3,710,399 A | 1/1973 | Hurst | |
| 3,893,448 A | 7/1975 | Brantigan | |
| 3,906,217 A | 9/1975 | Lackore | |
| 3,988,535 A | 10/1976 | Hickman et al. | |
| 4,047,136 A | 9/1977 | Satto | |
| 4,063,561 A | 12/1977 | McKenna | |
| 4,099,192 A | 7/1978 | Aizawa et al. | |
| 4,278,077 A | 7/1981 | Mizumoto | |
| 4,384,584 A | 5/1983 | Chen | |

(Continued)

FOREIGN PATENT DOCUMENTS

| | | |
|---|---|---|
| DE | 10149421 A1 | 4/2003 |
| JP | 2005261734 A | 9/2005 |

(Continued)

OTHER PUBLICATIONS

International Search Report, International Application No. PCT/US2010/051812, Mar. 21, 2011.

(Continued)

*Primary Examiner* — Katrina Stransky

(57) ABSTRACT

A surgical device comprises an elongate shaft comprising an outer tube and an inner rod positioned in the outer tube, the outer tube and inner rod each comprising a distal end and a proximal end. An actuator is operably connected to the proximal ends of the outer tube and the inner rod. An end effector is adapted for in vivo attachment to and detachment from the distal ends of the outer tube and the inner rod, the end effector comprising a collet for locking engagement with the distal end of the inner rod. The end effector may further comprise a second collet for locking engagement with the outer tube. The surgical device may further comprise a loader comprising a collet for locking the end effector in the loader.

12 Claims, 11 Drawing Sheets

(56) References Cited

U.S. PATENT DOCUMENTS

| | | |
|---|---|---|
| 4,585,282 A | 4/1986 | Bosley |
| 4,597,390 A | 7/1986 | Mulhollan et al. |
| 4,655,746 A | 4/1987 | Daniels et al. |
| 5,052,402 A | 10/1991 | Bencini et al. |
| 5,053,043 A * | 10/1991 | Gottesman et al. .......... 606/148 |
| 5,201,743 A | 4/1993 | Haber et al. |
| 5,282,806 A * | 2/1994 | Haber et al. ................ 606/139 |
| 5,286,255 A | 2/1994 | Weber |
| 5,308,357 A | 5/1994 | Lichtman |
| 5,314,424 A | 5/1994 | Nicholas |
| 5,330,502 A | 7/1994 | Hassler et al. |
| 5,352,219 A | 10/1994 | Reddy |
| 5,392,917 A | 2/1995 | Alpern et al. |
| 5,417,203 A | 5/1995 | Tovey et al. |
| 5,441,059 A | 8/1995 | Dannan |
| 5,468,250 A | 11/1995 | Paraschac et al. |
| 5,502,698 A | 3/1996 | Mochizuki |
| 5,507,297 A | 4/1996 | Slater et al. |
| 5,507,774 A * | 4/1996 | Holmes et al. .............. 606/208 |
| 5,540,648 A | 7/1996 | Yoon |
| 5,562,655 A | 10/1996 | Mittelstadt et al. |
| 5,578,052 A | 11/1996 | Koros et al. |
| 5,593,402 A * | 1/1997 | Patrick ............................ 606/1 |
| 5,613,937 A | 3/1997 | Garrison et al. |
| 5,618,303 A | 4/1997 | Marlow et al. |
| 5,632,764 A * | 5/1997 | Beideman et al. .......... 606/205 |
| 5,716,326 A | 2/1998 | Dannan |
| 5,718,714 A | 2/1998 | Livneh |
| 5,722,988 A | 3/1998 | Weisshaupt |
| 5,762,255 A | 6/1998 | Chrisman et al. |
| 5,782,748 A | 7/1998 | Palmer et al. |
| 5,792,165 A * | 8/1998 | Klieman et al. ............. 606/170 |
| 5,810,865 A | 9/1998 | Koscher et al. |
| 5,810,877 A | 9/1998 | Roth et al. |
| 5,881,615 A | 3/1999 | Dahl et al. |
| 5,893,875 A * | 4/1999 | O'Connor et al. ........... 606/205 |
| 5,928,263 A | 7/1999 | Hoogeboom |
| 5,980,455 A | 11/1999 | Daniel et al. |
| 6,024,748 A | 2/2000 | Manzo et al. |
| 6,059,719 A * | 5/2000 | Yamamoto et al. .......... 600/127 |
| 6,099,537 A | 8/2000 | Sugai et al. |
| 6,126,359 A * | 10/2000 | Dittrich et al. .............. 403/349 |
| 6,159,200 A | 12/2000 | Verdura et al. |
| 6,273,882 B1 | 8/2001 | Whittier et al. |
| 6,309,397 B1 * | 10/2001 | Julian et al. ................. 606/130 |
| 6,315,789 B1 | 11/2001 | Cragg |
| 6,419,688 B1 | 7/2002 | Bacher et al. |
| 6,471,172 B1 | 10/2002 | Lemke et al. |
| 6,589,211 B1 | 7/2003 | MacLeod |
| 6,595,984 B1 * | 7/2003 | DeGuillebon ..................... 606/1 |
| 6,626,824 B2 | 9/2003 | Ruegg et al. |
| 6,635,071 B2 | 10/2003 | Boche et al. |
| 6,663,641 B1 | 12/2003 | Kovac et al. |
| 6,666,875 B1 | 12/2003 | Sakurai et al. |
| 6,723,043 B2 | 4/2004 | Kleeman et al. |
| 6,770,081 B1 | 8/2004 | Cooper et al. |
| 6,776,165 B2 | 8/2004 | Jin |
| 6,814,742 B2 * | 11/2004 | Kimura et al. ............... 606/151 |
| 6,827,712 B2 | 12/2004 | Tovey et al. |
| 6,860,878 B2 * | 3/2005 | Brock .............................. 606/1 |
| 6,869,395 B2 | 3/2005 | Page et al. |
| 6,884,213 B2 | 4/2005 | Raz et al. |
| 6,936,003 B2 | 8/2005 | Iddan |
| 6,942,674 B2 | 9/2005 | Belef et al. |
| 6,986,738 B2 | 1/2006 | Glukhovsky et al. |
| 6,994,708 B2 | 2/2006 | Manzo |
| 7,039,453 B2 | 5/2006 | Mullick et al. |
| 7,042,184 B2 | 5/2006 | Oleynikov et al. |
| 7,066,879 B2 | 6/2006 | Fowler et al. |
| 7,083,579 B2 | 8/2006 | Yokoi et al. |
| 7,122,028 B2 * | 10/2006 | Looper et al. .................... 606/1 |
| 7,125,403 B2 * | 10/2006 | Julian et al. ..................... 606/1 |
| 7,169,104 B2 | 1/2007 | Ueda et al. |
| 7,199,545 B2 | 4/2007 | Oleynikov et al. |
| 7,211,094 B2 | 5/2007 | Gannoe et al. |
| 7,241,290 B2 | 7/2007 | Doyle et al. |
| 7,297,142 B2 | 11/2007 | Brock |
| 7,331,967 B2 | 2/2008 | Lee et al. |
| 7,429,259 B2 | 9/2008 | Cadeddu et al. |
| 7,448,993 B2 | 11/2008 | Yokoi et al. |
| 7,559,887 B2 | 7/2009 | Dannan |
| 7,566,331 B2 | 7/2009 | Looper et al. |
| 7,604,642 B2 | 10/2009 | Brock |
| 7,651,471 B2 | 1/2010 | Yokoi et al. |
| 7,666,181 B2 | 2/2010 | Abou El Kheir |
| 7,678,043 B2 | 3/2010 | Gilad |
| 7,691,103 B2 | 4/2010 | Fernandez et al. |
| 7,691,126 B2 * | 4/2010 | Bacher .......................... 606/205 |
| 7,699,835 B2 | 4/2010 | Lee et al. |
| 7,722,599 B2 | 5/2010 | Julian et al. |
| 7,862,553 B2 | 1/2011 | Ewaschuk |
| 7,894,882 B2 | 2/2011 | Mullick et al. |
| 7,901,398 B2 | 3/2011 | Stanczak et al. |
| 8,012,154 B2 | 9/2011 | Livneh |
| 8,021,358 B2 | 9/2011 | Doyle et al. |
| 8,038,612 B2 | 10/2011 | Paz |
| 8,052,636 B2 | 11/2011 | Moll et al. |
| 8,057,502 B2 | 11/2011 | Maliglowka et al. |
| 8,088,062 B2 | 1/2012 | Zwolinski |
| 8,114,098 B2 | 2/2012 | Kimura et al. |
| 8,128,643 B2 | 3/2012 | Aranyi et al. |
| 8,133,254 B2 | 3/2012 | Dumbauld et al. |
| 8,182,414 B2 | 5/2012 | Handa et al. |
| 8,187,166 B2 | 5/2012 | Kuth et al. |
| 8,353,897 B2 | 1/2013 | Doyle et al. |
| 8,377,044 B2 | 2/2013 | Coe et al. |
| 8,397,335 B2 | 3/2013 | Gordin et al. |
| 8,398,544 B2 | 3/2013 | Altamirano |
| 8,409,076 B2 | 4/2013 | Pang et al. |
| 8,475,361 B2 | 7/2013 | Barlow et al. |
| 8,518,024 B2 | 8/2013 | Williams et al. |
| 8,545,519 B2 | 10/2013 | Aguirre et al. |
| 8,636,648 B2 | 1/2014 | Gazdzinski |
| 8,721,539 B2 | 5/2014 | Shohat et al. |
| 8,758,391 B2 | 6/2014 | Swayze et al. |
| 8,764,735 B2 | 7/2014 | Coe et al. |
| 8,845,661 B2 | 9/2014 | D'Arcangelo et al. |
| 8,939,997 B2 | 1/2015 | Martinez et al. |
| 8,979,891 B2 | 3/2015 | McLawhorn et al. |
| 2002/0128645 A1 | 9/2002 | Messerly |
| 2002/0177843 A1 | 11/2002 | Anderson et al. |
| 2003/0114731 A1 | 6/2003 | Cadeddu et al. |
| 2003/0120272 A1* | 6/2003 | Schneider et al. ............ 606/49 |
| 2004/0093039 A1 | 5/2004 | Schumert |
| 2004/0152941 A1 | 8/2004 | Asmus et al. |
| 2004/0267254 A1 | 12/2004 | Manzo et al. |
| 2005/0033354 A1 | 2/2005 | Montalvo et al. |
| 2005/0119640 A1 | 6/2005 | Sverduk et al. |
| 2005/0131457 A1 | 6/2005 | Douglas et al. |
| 2005/0250984 A1 | 11/2005 | Lam et al. |
| 2005/0272972 A1 | 12/2005 | Iddan |
| 2005/0272974 A1 | 12/2005 | Iddan |
| 2005/0273139 A1 | 12/2005 | Krauss et al. |
| 2005/0288555 A1 | 12/2005 | Binmoeller |
| 2006/0079933 A1 | 4/2006 | Hushka et al. |
| 2006/0184161 A1* | 8/2006 | Maahs et al. ...................... 606/2 |
| 2006/0190035 A1 | 8/2006 | Hushka et al. |
| 2006/0258905 A1* | 11/2006 | Kaji et al. ..................... 600/106 |
| 2007/0010709 A1 | 1/2007 | Reinschke |
| 2007/0049966 A1 | 3/2007 | Bonadio et al. |
| 2007/0073247 A1* | 3/2007 | Ewaschuk ..................... 604/264 |
| 2007/0123748 A1 | 5/2007 | Meglan |
| 2007/0265502 A1* | 11/2007 | Minosawa et al. ........... 600/173 |
| 2007/0270651 A1 | 11/2007 | Gilad et al. |
| 2008/0004656 A1 | 1/2008 | Livneh |
| 2008/0015413 A1 | 1/2008 | Barlow et al. |
| 2008/0045003 A1 | 2/2008 | Lee et al. |
| 2008/0142005 A1 | 6/2008 | Schnell |
| 2008/0154299 A1* | 6/2008 | Livneh ........................... 606/205 |
| 2008/0208246 A1* | 8/2008 | Livneh ........................... 606/205 |
| 2008/0242939 A1* | 10/2008 | Johnston ........................ 600/204 |
| 2008/0243106 A1* | 10/2008 | Coe et al. .......................... 606/1 |
| 2009/0005638 A1* | 1/2009 | Zwolinski ..................... 600/106 |
| 2009/0171147 A1 | 7/2009 | Lee et al. |

(56) References Cited

U.S. PATENT DOCUMENTS

| | | | |
|---|---|---|---|
| 2009/0209946 A1* | 8/2009 | Swayze et al. | 606/1 |
| 2010/0198248 A1 | 8/2010 | Vakharia | |
| 2010/0249700 A1* | 9/2010 | Spivey | 604/96.01 |
| 2011/0040322 A1 | 2/2011 | Major | |
| 2011/0087224 A1 | 4/2011 | Cadeddu et al. | |
| 2011/0087265 A1* | 4/2011 | Nobis et al. | 606/205 |
| 2011/0087266 A1* | 4/2011 | Conlon et al. | 606/205 |
| 2011/0087267 A1* | 4/2011 | Spivey et al. | 606/205 |
| 2011/0208007 A1* | 8/2011 | Shohat et al. | 600/227 |
| 2011/0230869 A1 | 9/2011 | Altamirano | |
| 2011/0288560 A1 | 11/2011 | Shohat et al. | |
| 2012/0016391 A1* | 1/2012 | Aguirre et al. | 606/151 |
| 2012/0078290 A1* | 3/2012 | Nobis et al. | 606/206 |
| 2012/0078291 A1* | 3/2012 | Nobis et al. | 606/206 |
| 2012/0083778 A1* | 4/2012 | McGaffigan et al. | 606/28 |
| 2012/0083826 A1* | 4/2012 | Chao et al. | 606/205 |
| 2012/0109160 A1* | 5/2012 | Martinez et al. | 606/142 |
| 2012/0165863 A1* | 6/2012 | McLawhorn et al. | 606/207 |
| 2012/0259325 A1* | 10/2012 | Houser et al. | 606/33 |
| 2012/0289773 A1* | 11/2012 | Joshi et al. | 600/104 |
| 2012/0316575 A1* | 12/2012 | Farin et al. | 606/130 |
| 2013/0085337 A1* | 4/2013 | Hess et al. | 600/157 |
| 2013/0211196 A1* | 8/2013 | Belson et al. | 600/104 |
| 2014/0005474 A1 | 1/2014 | Farin et al. | |
| 2014/0066711 A1 | 3/2014 | Farin et al. | |
| 2014/0088569 A1* | 3/2014 | Parihar et al. | 606/1 |
| 2014/0088637 A1 | 3/2014 | Parihar et al. | |
| 2014/0088638 A1* | 3/2014 | Parihar | 606/206 |

FOREIGN PATENT DOCUMENTS

| | | |
|---|---|---|
| WO | WO 2010114634 A1 | 10/2010 |
| WO | WO 2011044353 A1 | 4/2011 |
| WO | WO 2011/089565 A1 | 7/2011 |
| WO | WO 2012040183 A1 | 3/2012 |
| WO | WO 2012/112622 | 8/2012 |
| WO | WO 2013007764 A2 | 1/2013 |
| WO | WO 2013048963 A2 | 4/2013 |
| WO | WO 2014/052177 | 4/2014 |

OTHER PUBLICATIONS

International Search Report, International Application No. PCT/US2011/050198, Mar. 2, 2012.
International Search Report, International Application No. PCT/US2011/05237, Dec. 12, 2011.
International Search Report, International Application No. PCT/US2012/056900, Apr. 3, 2013.
International Search Report, International Application No. PCT/US2013/060803, Feb. 1, 2014.
Co-Pending U.S. Appl. No. 12/576,514, filed Oct. 2, 2009, (Now Issued 8,623,011).
Co-Pending U.S. Appl. No. 12/576,529, filed Oct. 9, 2009.
Co-Pending U.S. Appl. No. 12/576,546, filed Oct. 9, 2009.
Co-Pending U.S. Appl. No. 12/576,565, filed Oct. 9, 2009.
Co-Pending U.S. Appl. No. 12/576,578, filed Oct. 9, 2009.
Co-Pending U.S. Appl. No. 12/617,998, filed Nov. 13, 2009 (Now US 2011/0115891).
Co-Pending U.S. Appl. No. 12/873,829, filed Sep. 1, 2010.
Co-Pending U.S. Appl. No. 12/873,845, filed Sep. 1, 2010.
Co-Pending U.S. Appl. No. 12/879,310, filed Oct. 9, 2010, (Now 2012/0065627).
Co-Pending U.S. Appl. No. 12/889,454, filed Sep. 24, 2010.
Co-Pending U.S. Appl. No. 12/889,458, filed Sep. 24, 2010.
Co-Pending U.S. Appl. No. 12/900,132, filed Jul. 10, 2010, (Now US 2012/0089093).
Co-Pending U.S. Appl. No. 12/902,531, filed Dec. 10, 2010, (Now US 2012/0088965).
Co-Pending U.S. Appl. No. 12/904,280, filed Oct. 14, 2010, (Now US 2012/0095298).
Co-Pending U.S. Appl. No. 13/249,790, filed Sep. 30, 2011.
Co-Pending U.S. Appl. No. 13/627,177, filed Sep. 26, 2012.
Co-Pending U.S. Appl. No. 13/627,192, filed Sep. 26, 2012.
Co-Pending U.S. Appl. No. 13/627,211, filed Sep. 26, 2012.
Co-Pending U.S. Appl. No. 13/779,211, filed Feb. 27, 2013.
Co-Pending U.S. Appl. No. 13/779,235, filed Feb. 27, 2013.
Co-Pending U.S. Appl. No. 13/779,254, filed Feb. 27, 2013.
Co-Pending U.S. Appl. No. 13/832,496, filed Mar. 15, 2013.
Co-Pending U.S. Appl. No. 12/413,479, filed Mar. 27, 2009.
Co-Owned U.S. Appl. No. 14/302,734, filed Jun. 12, 2014.
Co-Owned U.S. Appl. No. 14/557,588, filed Dec. 2, 2014.
International Preliminary Report dated Mar. 5, 2013; International Application No. PCT/US2011/050198.
International Preliminary Report dated Apr. 11, 2012; International Application No. PCT/US2010/051812.
International Preliminary Report dated Mar. 26, 2013; International Application No. PCT/US2011/052327.
International Preliminary Report dated Apr. 1, 2014; International Application No. PCT/US2012/056900.
International Preliminary Report dated Sep. 1, 2015; International Application No. PCT/US2014/015738.
International Search Report dated May 28, 2014; International Application No. PCT/US2014/015738.
International Preliminary Report dated Mar. 31, 2015; International Application No. PCT/US2013/060803.
Co-owned U.S. Appl. No. 14/840,779, filed Aug. 31, 2015.

* cited by examiner

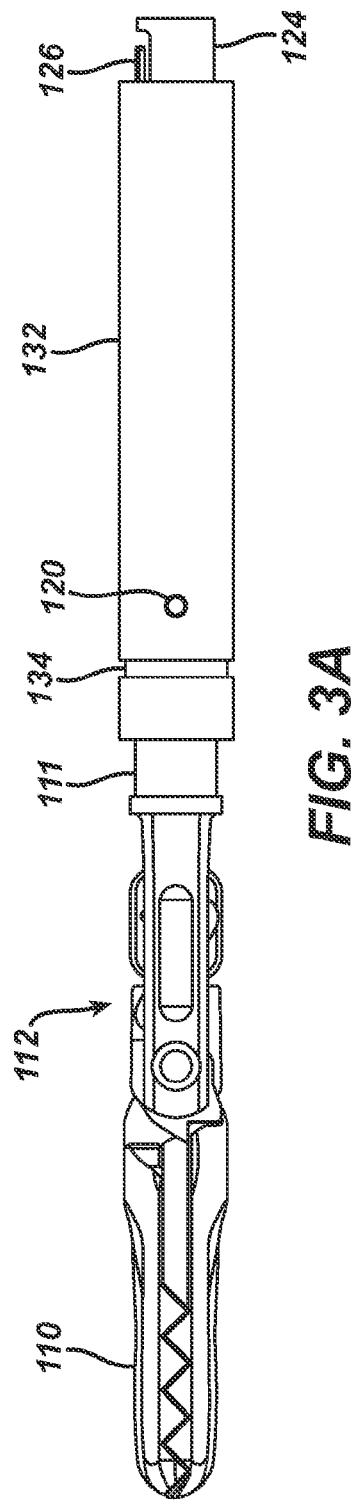
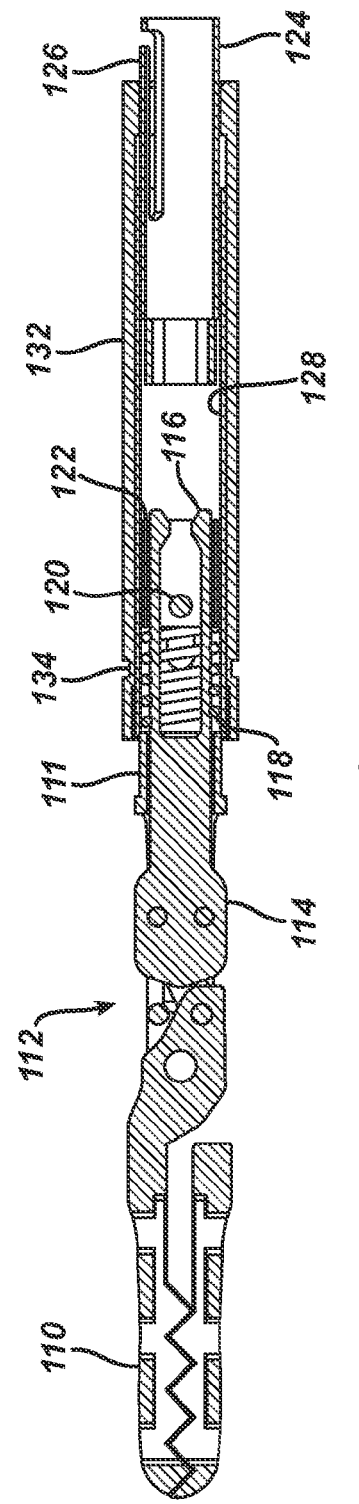

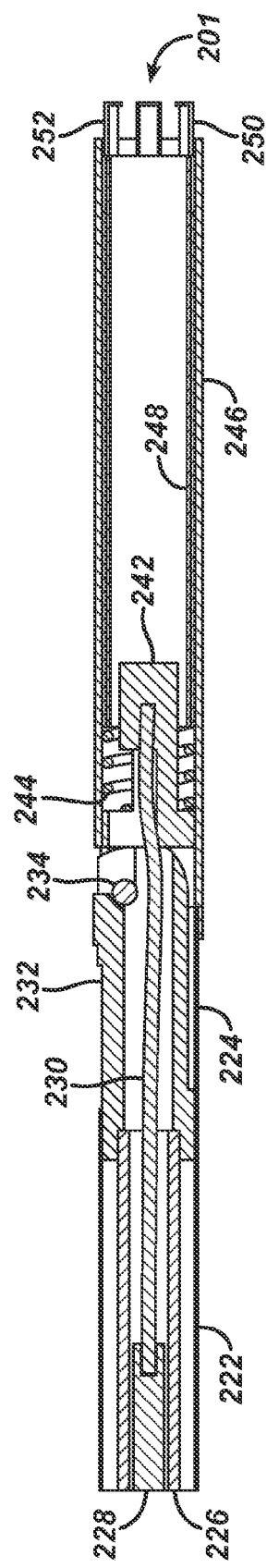
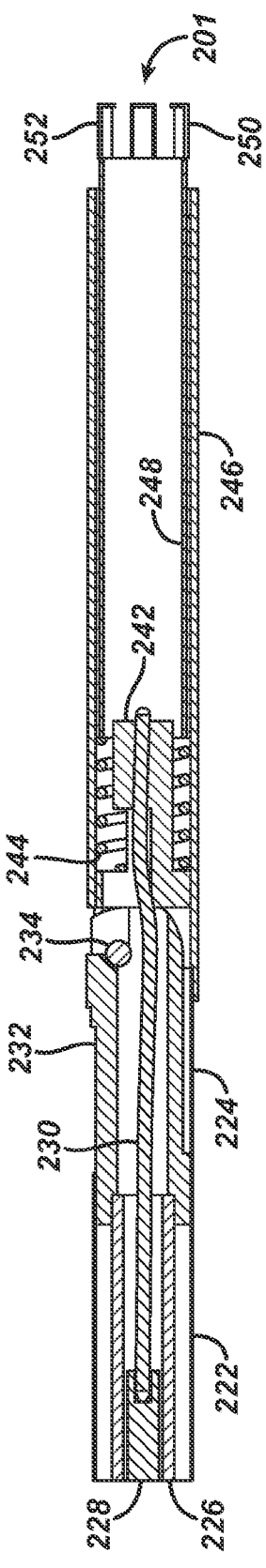
FIG. 6A
FIG. 6B

PERCUTANEOUS INSTRUMENT WITH COLLET LOCKING MECHANISMS

BACKGROUND

The present invention relates in general to surgical devices and procedures, and more particularly to minimally invasive surgery.

Surgical procedures are often used to treat and cure a wide range of diseases, conditions, and injuries. Surgery often requires access to internal tissue through open surgical procedures or endoscopic surgical procedures. The term "endoscopic" refers to all types of minimally invasive surgical procedures including laparoscopic, arthroscopic, natural orifice intraluminal, and natural orifice transluminal procedures. Endoscopic surgery has numerous advantages compared to traditional open surgical procedures, including reduced trauma, faster recovery, reduced risk of infection, and reduced scarring. Endoscopic surgery is often performed with an insufflatory fluid present within the body cavity, such as carbon dioxide or saline, to provide adequate space to perform the intended surgical procedures. The insufflated cavity is generally under pressure and is sometimes referred to as being in a state of pneumoperitoneum. Surgical access devices are often used to facilitate surgical manipulation of internal tissue while maintaining pneumoperitoneum. For example, trocars are often used to provide a port through which endoscopic surgical instruments are passed. Trocars generally have an instrument seal, which prevents the insufflatory fluid from escaping while an instrument is positioned in the trocar.

While a variety of different minimally invasive surgical devices are known, no one has previously made or used the surgical devices and methods in accordance with the present invention.

SUMMARY

In one embodiment a surgical device comprises an elongate shaft comprising a distal end and a proximal end. An actuator is operably connected to the proximal end of the elongate shaft. An end effector is adapted for attachment to and detachment from the distal end of the elongate shaft. The end effector comprises a laterally deflecting arm dimensioned to engage at least a portion of the distal end of the elongate shaft and a ring comprising a first axial position and a second axial position, wherein in the first position the arm can deflect laterally and in the second position the ring circumscribes the arm and constrains the arm from deflecting laterally.

The distal end of the inner rod may comprise a pointed tip. The actuator may comprise a manual handle. The end effector may be adapted for in vivo attachment and detachment from the distal end of the elongate shaft. The elongate shaft may be adapted for direct percutaneous insertion. The surgical device may further comprise a spring in the end effector biasing the ring to the second position. The ring first position may be is distal of the ring second position. The surgical device may further comprise a loader dimensioned for receiving end effector. The loader may comprise a locked state where the end effector is locked in the loader and the end effector ring is in its first position, and an unlocked state where the end effector is unlocked from the loader and the end effector ring is in its second position. The arm may comprise a medial tooth that engages a groove in the distal end of the elongate shaft.

In another embodiment, a surgical device comprises an elongate shaft comprising an outer tube and an inner rod positioned in the outer tube. The outer tube and inner rod each comprise a distal end and a proximal end. The inner rod and outer tube each comprise a groove on the distal end. An actuator is operably connected to the proximal ends of the outer tube and the inner rod. An end effector is adapted for in vivo attachment to and detachment from the distal ends of the outer tube and the inner rod. The end effector comprises a first arm dimensioned to engage the groove of the inner rod; a second arm dimensioned to engage the groove of the outer tube; an outer casing moveable between a distal axial position where the first and second arms can laterally deflect, and a proximal axial position where the first and second arms are constrained from laterally deflecting; and a spring biasing the outer casing to the proximal axial position.

The first and second arms may have a snap fit with the grooves on the inner rod and outer tube, respectively. The first and second arms may each be cantilevered and each comprise a medial tooth dimensioned to mate with the grooves on the inner rod and outer tube, respectively. The surgical device may further comprise a loader dimensioned for receiving end effector. The loader may comprise a locked state where the end effector is locked in the loader and the end effector outer casing is in its distal axial position, and an unlocked state where the end effector is unlocked from the loader and the end effector outer casing is in its proximal axial position. The surgical device may further comprise a second inner laterally deflecting arm dimensioned to engage the groove of the inner rod.

In yet another embodiment, a surgical device comprises an elongate shaft comprising an outer tube and an inner rod positioned in the outer tube, the outer tube and inner rod each comprising a distal end and a proximal end. An actuator is operably connected to the proximal ends of the outer tube and the inner rod. An end effector is adapted for in vivo attachment to and detachment from the distal ends of the outer tube and the inner rod, the end effector comprising a collet for locking engagement with the distal end of the inner rod. The end effector may further comprise a second collet for locking engagement with the outer tube. The surgical device may further comprise a loader comprising a collet for locking the end effector in the loader.

In another embodiment, a loader for facilitating in vivo attachment and detachment of an end effector to an instrument shaft comprises an elongate shaft having a distal end and a proximal end. A loader tube is connected to the distal end of the elongate shaft, the loader tube comprising a distal opening. A collet is positioned in the loader tube, the collet being adapted and sized to receive and engage the end effector inserted through the distal opening. The collet has a locked position relative the loader tube and an unlocked position relative the loader tube. An actuator is connected to the proximal end of the elongate shaft and is operative to select between the locked and unlocked positions.

The loader may further comprise a spring positioned in the loader tube biasing the collet to the unlocked position. A surgical system may comprise the loader; a instrument shaft adapted for direct percutaneous insertion; and an end effector adapted for in vivo attachment to and detachment from the instrument shaft. The end effector may be adapted to engage the instrument shaft in a locked state and an unlocked state. When the collet receives and engages the end effector in the locked position, the end effector may be in the unlocked state; and when the collet receives and engages the end effector in the unlocked position, the end effector may be in the locked state. The collet may be operatively connected to the end effector to switch the end effector between the locked and unlocked states. The loader tube may articulate relative the elongate shaft. The collet in the loader tube may comprise a plurality of cantilevered arms with medially oriented teeth. The teeth may be adapted and sized to engage a circumferential groove in the end effector.

In still another embodiment, a loader for facilitating in vivo attachment and detachment of an end effector to an instrument shaft comprises an elongate shaft having a distal end and a proximal end. A loader tube comprises a proximal end connected to the distal end of the elongate shaft and a distal opening. The loader comprises a means for locking and unlocking the end effector in the loader tube. An actuator is connected to the proximal end of the elongate shaft, the actuator being operatively connected to the means for locking and unlocking.

In another embodiment, a loader for facilitating in vivo attachment and detachment of an end effector to an instrument shaft comprises an elongate shaft having a distal end and a proximal end. A loader tube is connected to the distal end of the elongate shaft. The loader tube comprises a distal opening and a collet positioned in the loader tube. The collet being adapted and sized to receive and engage the end effector inserted through the distal opening. The collet having a first position locking the end effector in the loader tube and a second position in which the end effector can be withdrawn from the loader tube.

BRIEF DESCRIPTION OF DRAWINGS

While the specification concludes with claims which particularly point out and distinctly claim the invention, it is believed the invention will be better understood from the following description taken in conjunction with the accompanying drawings illustrating some non-limiting examples of the invention. Unless otherwise indicated, the figures are not necessarily drawn to scale, but rather to illustrate the principles of the invention.

FIG. 3 depicts side and cross-sectional views of an end effector;

FIG. 6A depicts an cross-sectional view of a loader tube in its locked position;

FIG. 6B depicts an cross-sectional view of a loader tube in its unlocked position;

DETAILED DESCRIPTION

Figure 1:
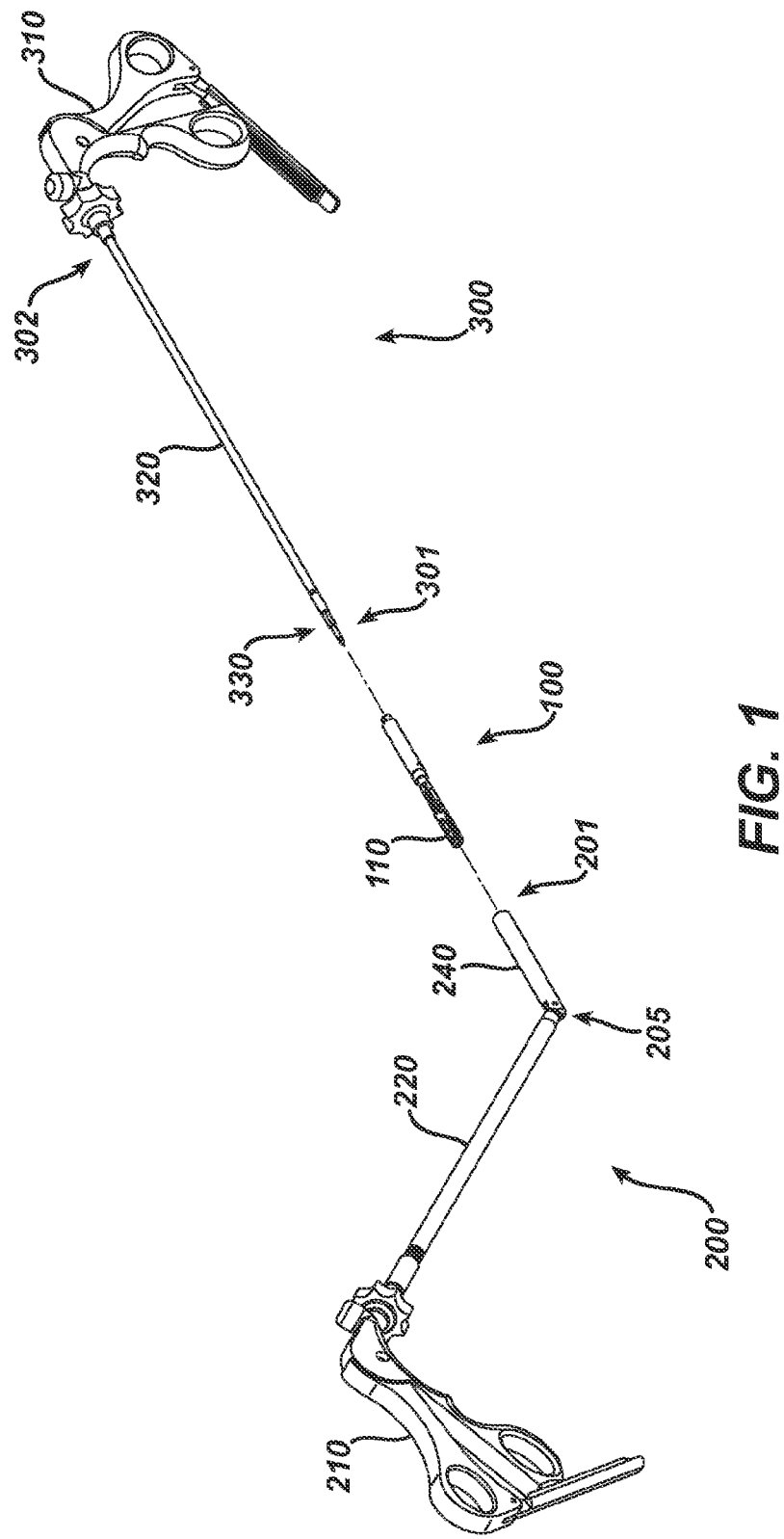
FIG. 1 depicts a surgical instrument with end effector, control shaft, and loader.

FIG. 1 illustrates one example of a surgical system. A instrument shaft (300) may comprise an elongate shaft (320) having a distal end (301) and a proximal end (302). The elongate shaft (320) may be rigid and adapted for insertion into a body cavity through an access device, such a trocar, or through direct percutaneous insertion without an access device. The elongate shaft (320) may comprise two or more coaxially nested shafts that move relative one another in response to inputs from the actuator (310).

The actuator (310) is operably connected to the proximal end (302) of the shaft (320). In this embodiment the actuator (310) is a manual pistol grip handle; however, a variety of other manual actuators could also be used, including a scissor grip handle, a syringe grip handle, endoscopic rotary knobs, and the like. The actuator (310) could also take the form of a robotic interface, such as an DAVINCI puck, a housing comprising gears or pulleys, servomechanisms, and the like.

The end effector (100) is adapted for in vivo attachment to and detachment from the elongate shaft (320). The attachment/detachment mechanism includes mating features (330) that engage corresponding collet features in the end effector (100). Relative movement of the coaxially nested shafts actuate the end effector (100).

The end effector (100) in this embodiment includes a pair of surgical jaws (110) having an opened position and closed position. In this embodiment, the jaws (110) are shown as a grasper; however, a variety of other tissue manipulating jaws could also be used, including dissectors, sheers, babcocks, forceps, staplers, clip appliers, and the like. Non-jawed end effectors (100) could also be employed such as hook knives, snares, retractors, and the like. In the case of end effectors that require energy, appropriate energy transmission mechanisms known in the art may be added. For instance, appropriate electrical connections may be added between the shaft (320) and end effector (100) to enable bi-polar forceps. Similarly, an ultrasonic transducer and waveguide may be added for the ultrasonic shears end effector.

A loader (200) may be used to introduce the end effector (100) into a patient's body cavity, typically through an access port, and to facilitate its attachment and detachment of the end effector (100) to the elongate shaft (320). The loader tube (240) receives the end effector (100) through its distal end (201). The loader (200) may comprise an actuator (210), an elongate shaft (220), and loader tube (240). In this embodiment the actuator (210) is a manual pistol grip handle; however, a variety of other manual actuators could also be used, including a scissor grip handle, a syringe grip handle, endoscopic rotary knobs, and the like. The actuator (210) could also take the form of a robotic interface, such as an DAVINCI puck, a housing comprising gears or pulleys, servomechanisms, and the like. The actuator (210) is operable to articulate the loader tube (240) relative the shaft (220) about the joint (205), as well as to lock and unlock the loader tube (240).

Figure 2:
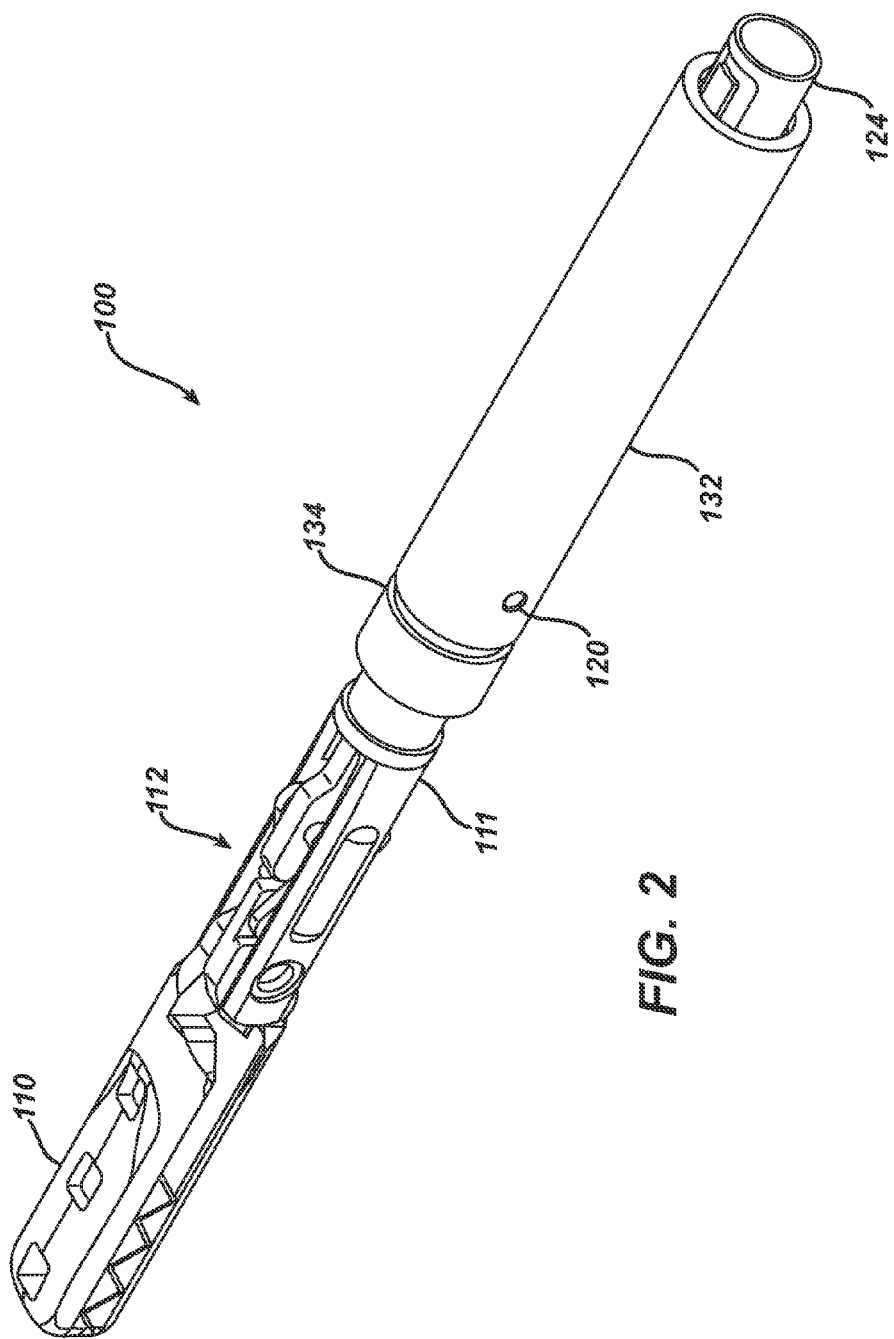
FIG. 2 depicts a perspective view on an end effector.
Figure 4:
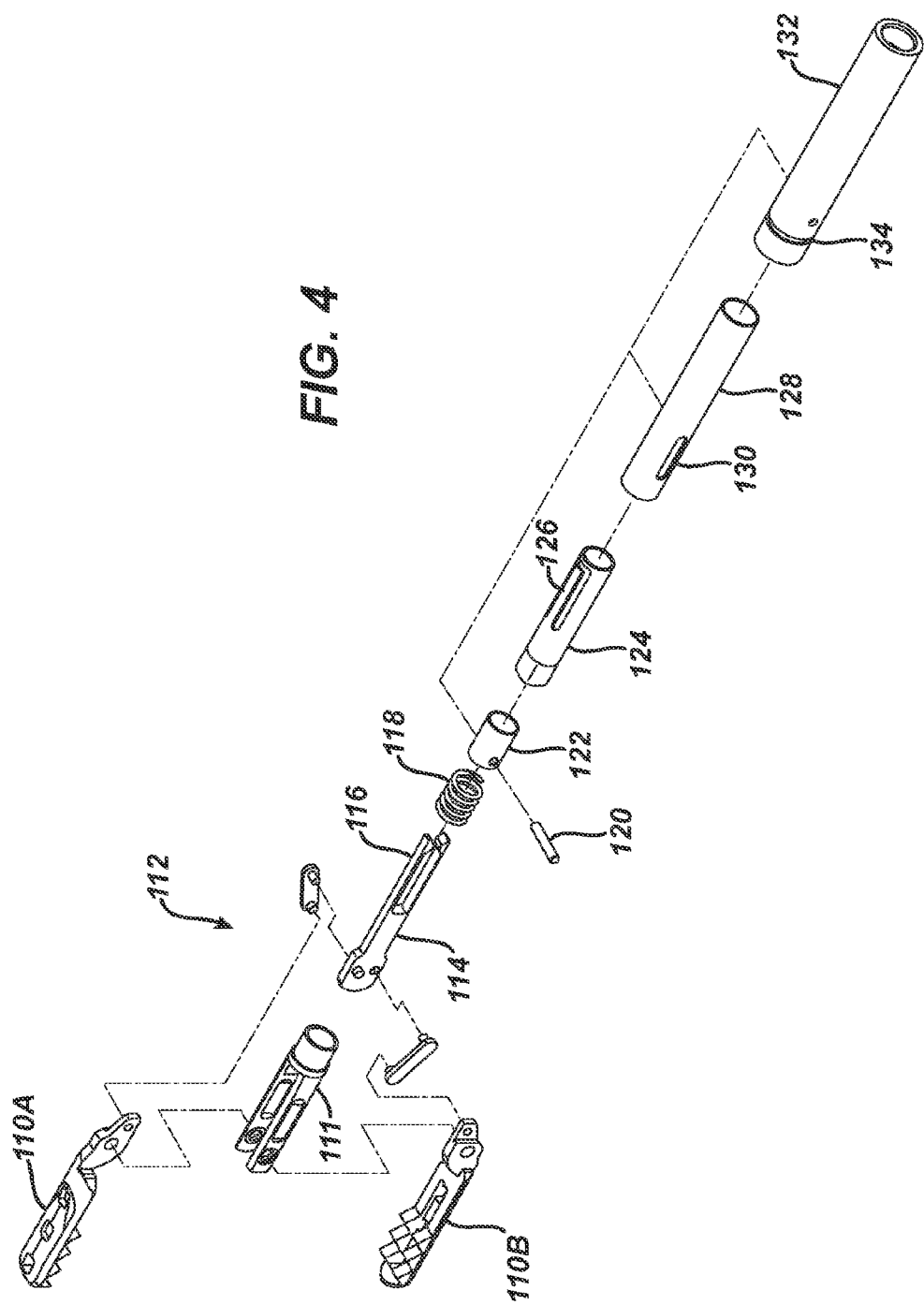
FIG. 4 depicts an exploded view of an end effector.

FIGS. 2-4 illustrate one embodiment of an end effector (100). The end effector (100) comprises a pair of jaws (110A, B) that pivot relative the clevis (111). The driver (114) is connected to the jaws (110A, B) by links (112), so axial motion of the driver (114) relative the clevis (111) will cause the jaws (110A, B) to move between their open and closed positions. The clevis (111) and the tube (124) are both axially fixed to the inner casing (128) as an inner sub-assembly.

The outer casing (132) is generally tubular in shape and comprises a circumferential groove (134). The pin (120) axially fixes the collar (122) to the outer casing (132) as an outer sub-assembly. The inner and outer sub-assemblies are coaxially nested relative one another. The pin (120) travels in the slot (130) thus facilitating axial movement of the outer sub-assembly between a distal position and a proximal position relative the inner sub-assembly. As shown in FIGS. 2 and 3, the outer sub-assembly is in its proximal position. The slot (130) may define the axial stroke limit of the outer sub-assembly. The spring (118) is interposed between the clevis (111) and the collar (122) and biases the outer sub-assembly to its proximal position.

The driver (114) and tube (124) each comprise a collet mechanism to selectively engage and hold the corresponding mating features (330) on the elongate shaft (320). In this embodiment, the driver (114) comprises a pair of cantilevered arms (116) each having a medially oriented cleat or tooth on the proximal end. The tube (124) comprises a cantilevered arm (126) with a medially oriented cleat or tooth. The number and configuration of the arms (116, 126) may vary. When the outer sub-assembly is in its distal position, the arms (116) may resiliently deflect laterally. Similarly, the arm (126) may resiliently deflect laterally. When the outer sub-assembly is in its proximal position, the collar (122) circumscribes and constrains the arms (116) to their medial position and prevents them from lateral deflecting. Similarly, the outer casing (132) circumscribes and constrains the arm (126) to its medial position and prevents it from lateral deflecting. When the outer sub-assembly is in its distal position, the end effector (100) may be considered in its unlocked position, and when outer sub-assembly is in its proximal position the end effector (100) may be considered in its locked position.

Figure 5:
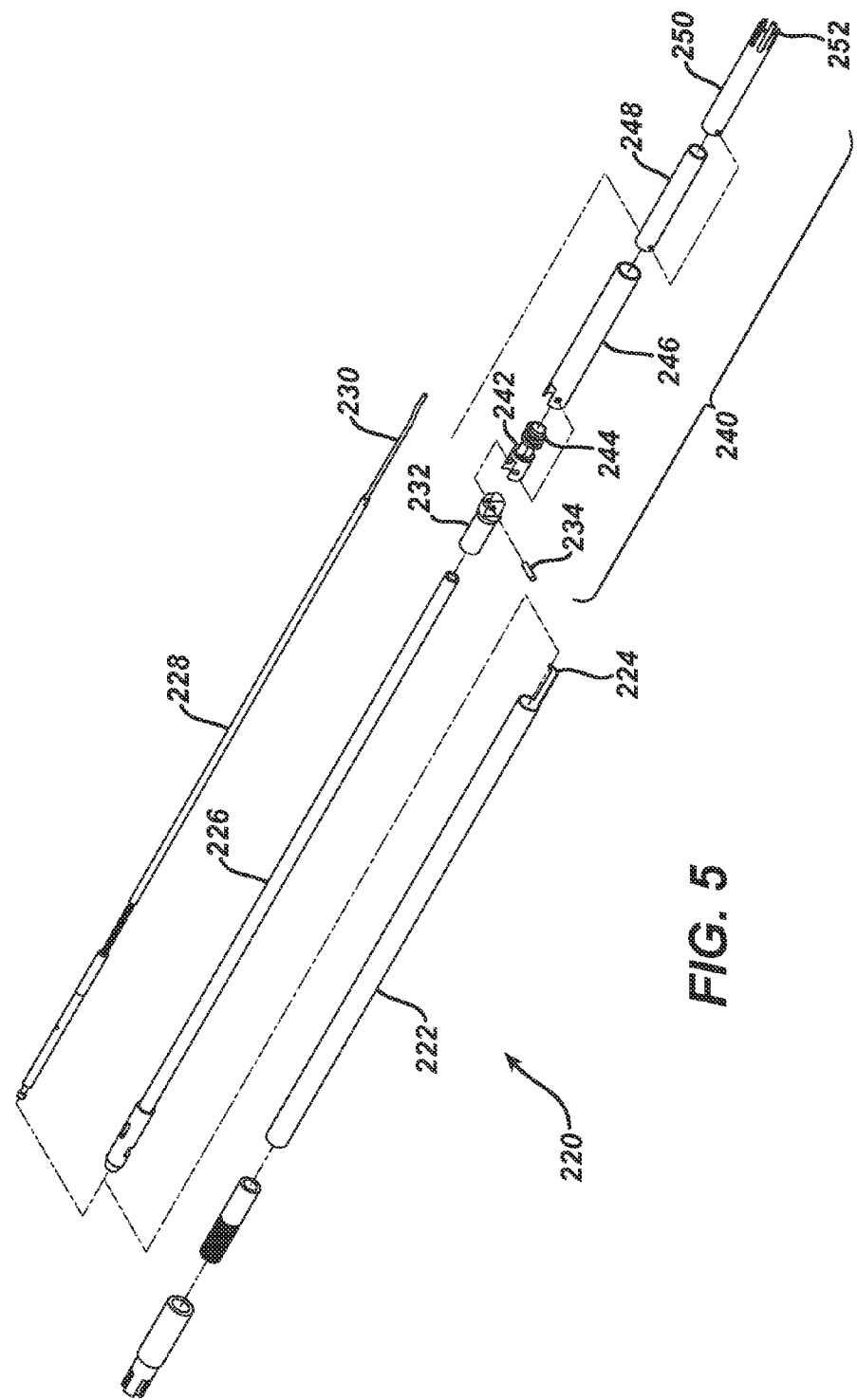
FIG. 5 depicts an exploded view of a loader shaft.

FIGS. 5-6 illustrate one embodiment of a loader (200). In this embodiment, the shaft (220) comprises a plurality of co-axially arranged rods, including an outer tube (222), an inner tube (226), and an inner rod (228) each operably connected to the actuator (210). The inner tube (226) is axially fixed to the proximal hinge component (232). The outer housing (246) is axially fixed to the distal hinge component (242). The proximal hinge component (232) is connected to the distal hinge component (242) by the pin (234) as the axis of the hinge articulation. Outer tube (222) comprises a distal extension (224) connected to the outer housing (246), so axial movement of the outer tube (222) relative to the inner tube (226) will cause the loader tube (240) to articulate.

The loader tube (240) comprises a collet mechanism to selectively engage and hold the end effector (100). In this embodiment an inner locking tube (248) and outer locking tube (250) are axially fixed to one another as a locking sub-assembly. The locking sub-assembly is coaxially nested within outer housing (246) and can slide axially between a distal position and a proximal position. The spring (244) is interposed between the distal hinge component (242) and the locking sub-assembly, and biases the locking sub-assembly to its distal position. The flexible extension (230) of the inner rod (228) is slideably positioned through the hinge components (232, 242) and is axially fixed to the locking sub-assembly. Pulling the inner rod (228) proximally relative the inner tube (226) will similarly pull the locking sub-assembly proximally and compress the spring (244).

The outer locking tube (250) comprises a plurality of arms (252) with a medially oriented cleats or teeth. The number and configuration of the arms (252) may vary. When the locking sub-assembly is in its proximal position, the arms (252) may resiliently deflect laterally. Optionally, the arms (252) may be biased laterally outward. When the locking sub-assembly is in its distal position, the outer housing (246) circumscribes and constrains the arms (252) to their medial position and prevents them from deflecting laterally. When the locking sub-assembly is in its proximal position, the loader tube (240) may be considered in its the unlocked position, and when locking sub-assembly is in its distal position the loader tube (240) may be considered in its locked position.

Figure 7:
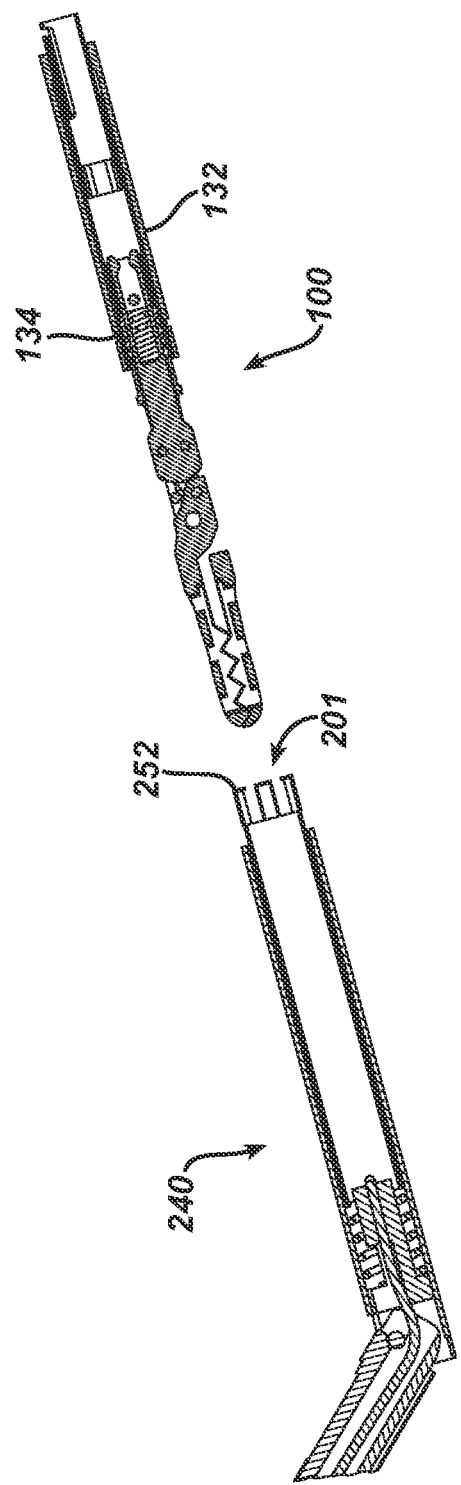
FIG. 7 depicts an cross-sectional view of a loader tube and an end effector.

FIGS. 7-11 illustrate a sequence of the instrument being introduced for use in the surgical field. FIG. 7 illustrates the loader tube (240) in its unlocked position ready to receive the end effector (100). The end effector (100) may be slid into the loader tube (240) until the cleats or teeth of the arms (252) align with the circumferential groove (134).

Figure 8:
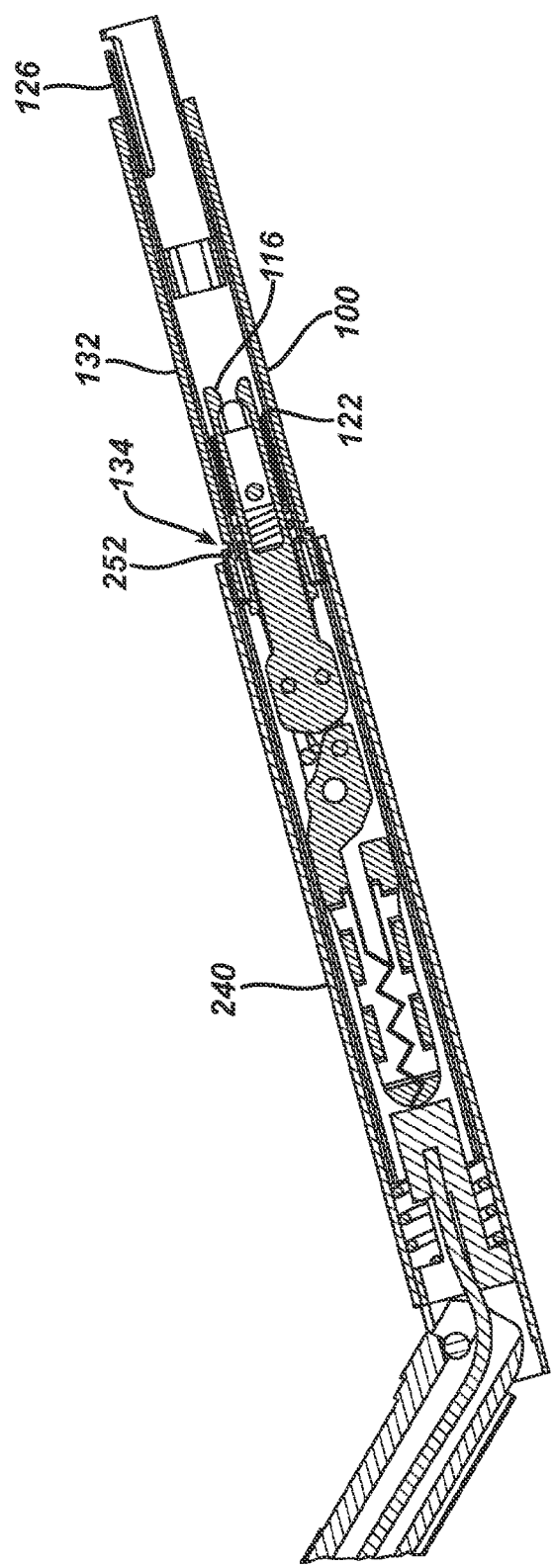
FIG. 8. depicts an cross-sectional view of an end effector locked in a loader tube.

As shown in FIG. 8, when the locking sub-assembly is pulled proximally so the loader tube (240) is in its locked position, the cleats or teeth of the arms (252) engage the circumferential groove (134) and lock the end effector into the loader tube (240). Simultaneously, the cleats or teeth of the arms (252) will pull the outer casing (132) distally so the end effector (100) is in its unlocked position. Accordingly, the arms (116, 126) are able to deflect laterally. This configuration is well suited to introduce the end effector (100) into the patient body cavity, typically through an access device in a non-articulated position.

Figure 9:
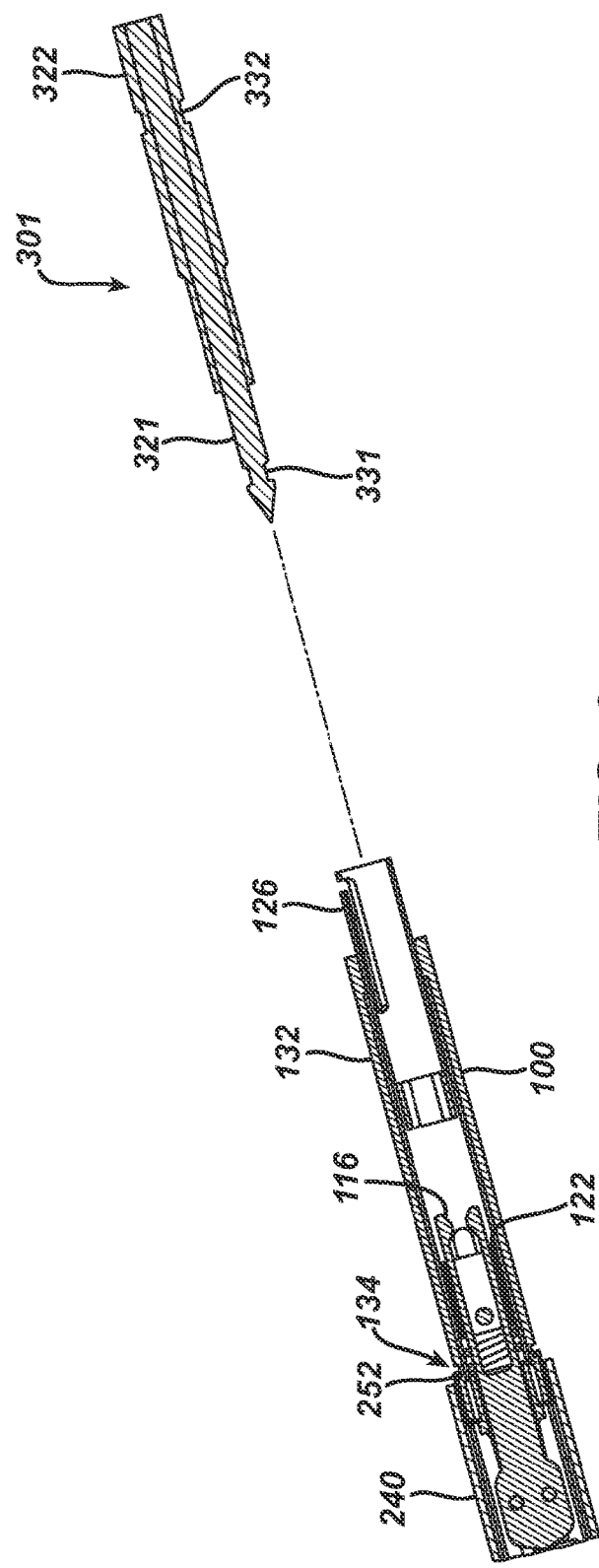
FIG. 9. depicts an cross-sectional view of an end effector locked in a loader tube and a control shaft.

As shown in FIG. 9, the distal end (301) of the elongate shaft (320) can be introduced into the patient body cavity, either through an access device or through direct percutaneous insertion. For direct percutaneous insertion uses, the elongate shaft (320) may be less than about 3 mm in diameter. In this embodiment the elongate shaft (320) comprises only two rods: an outer tube (322) and an inner rod (321). The outer tube (322) and an inner rod (321) are coaxially nested and can slide relative one another in response to inputs to the actuator (310). The outer tube (322) comprises a circumferential groove (332) dimensioned to receive the cleat or tooth of the arm (126). The inner rod (321) comprises a circumferential groove (331) dimensioned to receive the cleats or teeth of the arms (116). Optionally, the distal tip of the inner rod (321) may be pointed to facilitate direct percutaneous insertion.

Figure 10:
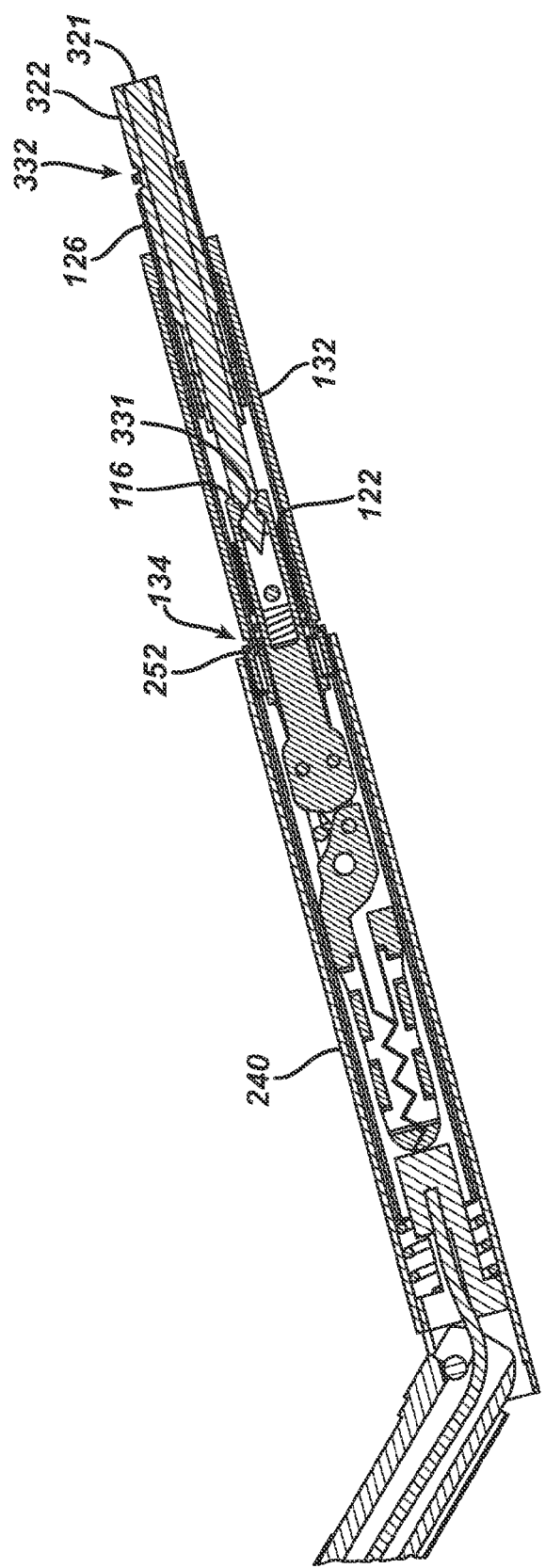
FIG. 10 depicts an cross-sectional view of an end effector locked in a loader tube and a control shaft provisionally attached to the end effector.

As shown in FIG. 10, the distal end (301) of the elongate shaft (320) can be inserted into the end effector (100) till the cleats or teeth of the arms (116, 126) resiliently deflect laterally and then snap into the grooves (331, 332), respectively. In this configuration, the end effector (100) is provisionally attached to, but not locked onto, the elongate shaft (320).

Figure 11:
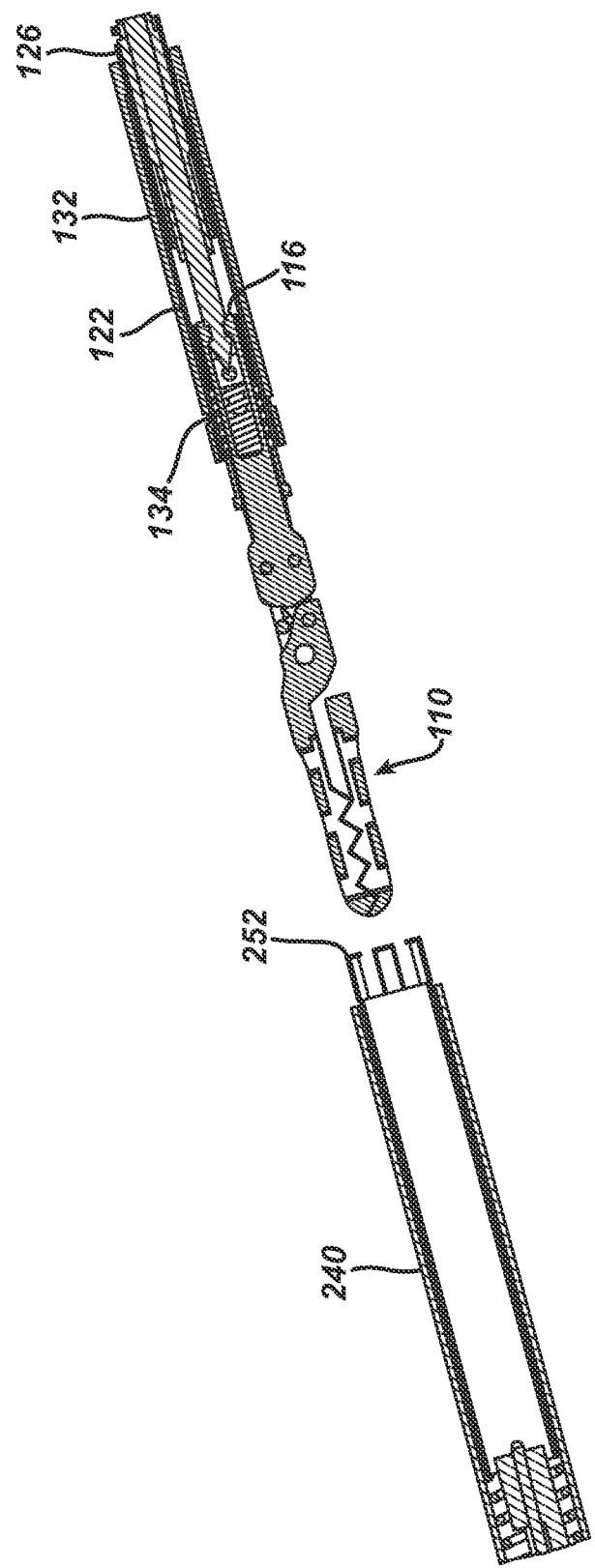
FIG. 11 depicts an cross-sectional view of an end effector locked onto a control shaft and separated from a loader.

As shown in FIG. 11, loader tube (240) can be moved to its unlocked position in response to inputs from the actuator so the arms (252) disengage from the groove (134), thus allowing the end effector (100) to be withdrawn from the loader tube (240). Simultaneously, the spring loaded outer housing (132) will bias proximally, thus locking the end effector (100) onto the distal end (301) of the elongate shaft (320). Through operation of the actuator (310), the inner rod (321) may be slid axially relative the outer tube (322), which will in turn slide the driver (114) relative the clevis (111) to open and close the jaws (110) so tissue may be manipulated during surgical procedures. The instrument can then be removed from the surgical field by reversing the sequence of FIGS. 7-11.

Having shown and described various embodiments and examples of the present invention, further adaptations of the methods and devices described herein can be accomplished by appropriate modifications by one of ordinary skill in the art without departing from the scope of the present invention. Several of such potential modifications have been mentioned, and others will be apparent to those skilled in the art. For instance, the specific materials, dimensions, and the scale of drawings will be understood to be non-limiting examples. Accordingly, the scope of the present invention should be considered in terms of the following claims and is understood not to be limited to the details of structure, materials, or acts shown and described in the specification and drawings.

The invention claimed is:

1. A surgical device, comprising:
   a) an elongate shaft comprising a distal end and a proximal end;
   b) an actuator operably connected to the proximal end of the elongate shaft;
   c) an end effector adapted for attachment to and detachment from the distal end of the elongate shaft, the end effector comprising:
      i) a laterally deflecting arm dimensioned to engage at least a portion of the distal end of the elongate shaft;
      ii) a ring comprising a first axial position and a second axial position, wherein in the first position the arm can deflect laterally and in the second position the ring circumscribes the arm and constrains the arm from deflecting laterally; and
      iii) a spring biasing the ring to the second position.

2. The surgical device of claim 1, wherein the actuator comprises a manual handle.

3. The surgical device of claim 1, wherein the end effector is adapted for in vivo attachment and detachment from the distal end of the elongate shaft.

4. The surgical device of claim 1, wherein the elongate shaft is adapted for direct percutaneous insertion.

5. The surgical device of claim 1, wherein the ring first position is distal of the ring second position.

6. The surgical device of claim 1, further comprising a loader dimensioned for receiving the end effector, the loader comprising:
   a locked state where the end effector is locked in the loader and the end effector ring is in its first position;
   an unlocked state where the end effector is unlocked from the loader and the end effector ring is in its second position.

7. The surgical device of claim 1, wherein the arm comprises a medial tooth that engages a groove in the distal end of the elongate shaft.

8. A surgical device, comprising:
   a) an elongate shaft comprising an outer tube and an inner rod positioned in the outer tube, the outer tube and inner rod each comprising a distal end and a proximal end, the inner rod and outer tube each comprising a groove on the distal end;
   b) an actuator operably connected to the proximal ends of the outer tube and the inner rod;
   c) an end effector adapted for in vivo attachment to and detachment from the distal ends of the outer tube and the inner rod, the end effector comprising:
      i) a first arm dimensioned to engage the groove of the inner rod;
      ii) a second arm dimensioned to engage the groove of the outer tube;
      iii) an outer casing moveable between a distal axial position where the first and second arms can laterally deflect, and a proximal axial position where the first and second arms are constrained from laterally deflecting; and
      iv) a spring biasing the outer casing to the proximal axial position.

9. The surgical device of claim 8, wherein the first and second arms have a snap fit with the grooves on the inner rod and outer tube, respectively.

10. The surgical device of claim 8, wherein the first and second arms are each cantilevered and each comprise a medial tooth dimensioned to mate with the grooves on the inner rod and outer tube, respectively.

11. The surgical device of claim 8, further comprising a loader dimensioned for receiving end effector, the loader comprising:
   a locked state where the end effector is locked in the loader and the end effector outer casing is in its distal axial position;
   an unlocked state where the end effector is unlocked from the loader and the end effector outer casing is in its proximal axial position.

12. The surgical device of claim 8, further comprising a second inner laterally deflecting arm dimensioned to engage the groove of the inner rod.

* * * * *